United States Patent [19]

Matsumoto et al.

[11] Patent Number: 4,861,917

[45] Date of Patent: Aug. 29, 1989

[54] PROCESS FOR PREPARING MACROCYCLIC 2-HALOGENOKETONES

[75] Inventors: Masakatsu Matsumoto, Sagamihara; Tamotsu Fujimoto, Yamato; Emiko Ejiri, Sagamihara, all of Japan

[73] Assignees: Sagami Chemical Research Center; Nippon Mining Company, Limited, both of Tokyo, Japan

[21] Appl. No.: 191,258

[22] Filed: May 6, 1988

[30] Foreign Application Priority Data

May 7, 1987 [JP] Japan ................... 62-109801

[51] Int. Cl.$^4$ ............................................. C07C 45/63
[52] U.S. Cl. ............................................. 568/347

[58] Field of Search ............ 568/347, 392, 375; 570/248

[56] References Cited

PUBLICATIONS

House, "Modern Synthetic Reactions", pp. 452–465 (1972), W. A. Benjamin, Inc.

Leonard et al., J.A.C.S., vol. 80, pp. 6039–6041 (1958).

Primary Examiner—James H. Reamer
Attorney, Agent, or Firm—Oblon, Spivak, McClelland, Maier & Neustadt

[57] ABSTRACT

Macrocyclic 2-halogenoketones are prepared by reacting a macrocyclic 2-hydroxyketone with a halogenating agent. This reaction may be carried out in the presence of a solvent and/or a catalyst.

16 Claims, No Drawings

PROCESS FOR PREPARING MACROCYCLIC 2-HALOGENOKETONES

BACKGROUND OF THE INVENTION

1. Field of the Invention

This invention relates to a process for efficiently preparing macrocyclic 2-halogenoketones, such as 2-halogenocyclopentadecanone, which are important as starting materials for the synthesis of high-grade perfumes typified by muscone.

2. Description of the Prior Art

It is conventionally known that macrocyclic 2-halogenoketones, such as 2-halogenocyclopentadecanone, can be prepared by oxidizing cyclopentadecanone with a molecular halogen. For example, there have been proposed processes involving the oxidation of cyclopentadecanone with $Br_2$ [L. Ruzicka & M. Stoll, Helv. Chim. Acta, 17, 1308 (1934); Japanese Patent Laid-Open No. 48635/'76] and involving the bromination of 1-acetoxy-1-cyclopentadecene [N. J. Leonard & F. H. Owens, J. Am. Chem. Soc., 80, 6039, (1958)].

However, these processes have the disadvantage that cyclopentadecanone used as the starting material is expensive and that bromine used as the oxidizing agent must be handled with great care for safety.

SUMMARY OF THE INVENTION

The present invention has been made in view of the above-described disadvantage of the prior art processes for preparing macrocyclic 2-halogenoketones. Accordingly, it is an object of the present invention to provide a process for preparing macrocyclic 2-halogenoketones efficiently and inexpensively.

According to the present invention, there is provided a process for preparing macrocyclic 2-halogenoketones of the general formula

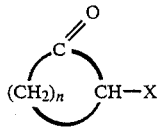

(I)

where X is a halogen atom and n is a whole number of 10 to 16, which comprises reacting a macrocyclic 2-hydroxyketone of the general formula

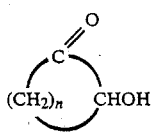

(II)

where n is a whole number of 10 to 16, with a halogenating agent.

DETAILED DESCRIPTION OF THE PREFERRED EMBODIMENTS

The macrocyclic 2-hydroxyketones (e.g., 2-hydroxycyclopentadecanone) within the scope of the general formula (II), which can be used as the starting material in the process of the present invention, may be readily prepared by the so-called acyloin condensation of alkane dioic acid diesters having the corresponding number of carbon atoms. It is should noted in this connection that, since 2-hydroxycyclopentadecanone is a raw material for the synthesis of cyclopentadecanone that has been used as the starting material in the prior art processes [the procedures for synthesis of cyclopentadecanone are described, for example, in V. V. Dhekne et al., Indian J. Chem., 353 (1967)], 2-hydroxycyclopentadecanone is cheaper and more readily available than cyclopentadecanone.

The halogenating agents which can be used in the halogenation of the aforesaid macrocyclic 2-hydroxyketones such as 2-hydroxycyclopentadecanone include, for example, hydrobromic acid, hydrochloric acid, phosphorus tribromide, phosphorus oxychloride, phosphorus pentachloride, thionyl chloride and thionyl bromide. Among these compounds, hydrobromic acid is preferred from the viewpoint of economy and reaction efficiency. The halogenating agent is preferably used in an amount of about 1 to 50 moles per mole of the 2-hydroxyketone.

In the process of the present invention, the reaction of the macrocyclic 2-hydroxyketone with the above-defined halogenating agent is preferably carried out in the presence of a solvent. Useful solvents include, for example, aromatic hydrocarbons such as benzene, toluene and xylene; and halogenated hydrocarbons such as dichloromethane and trichloroethane. Two-phase solvents composed of such an organic solvent and an aqueous medium are also useful. In addition, the reaction is carried out under an atmosphere of an inert gas such as argon.

Although the reaction temperature can range from room temperature to about 120° C., it is preferable from the viewpoint of reaction efficiency to employ a reaction temperature in the range of about 80° to 110° C. Moreover, the above-described reaction may be carried out in the presence of a catalyst comprising zinc sulfate. Where the catalyst is used, it is preferably used in an amount of about 0.2 to 2 moles per mole of the 2-hydroxyketone. The reaction time may generally range from about 2 to 30 hours.

As described above, the present invention makes it possible to obtain macrocyclic 2-halogenoketones easily by reacting a relatively cheap and readily available starting material with a halogenating agent and, therefore, is beneficial for the production of high-grade perfumes, such as muscone which is synthesized by using 2-halogenoketones as starting materials.

The present invention is further illustrated by the following examples.

EXAMPLE 1

Under an atmosphere of argon gas, a mixture composed of 103 mg (0.43 mmol) of 2-hydroxycyclopentadecanone, 5 ml of 47% hydrobromic acid and 5 ml of toluene was refluxed with stirring for 23 hours. After being cooled to room temperature, the reaction mixture was diluted with ether and the resulting organic phase was separated. This organic phase was washed with water and a saturated sodium chloride solution, and then dried over anhydrous magnesium sulfate.

The above organic phase was filtered, concentrated and then subjected to thin-layer chromatography using a 1:9 mixture of ether and hexane. Thus, there was obtained 90 mg (69% yield) of 2-bromocyclopentadecanone.

IR spectrum ($cm^{-1}$): 2950, 2870, 1715, 1460, 1440.
Mass spectrum (m/Z, %): 304(1.0) 303(1.1), 302($M^+$, 1.1), 223 (15.8), 98(47.9), 95(16.4), 83(23.1), 69(34.6), 67(24.2), 55(88.8), 43(39.1), 41(100).

$^1$H-NMR spectrum (400 MHz, CDCl$_3$, δppm, TMS): 1.25–1.39(m, 20H), 1.67(m, 2H), 1.96(m, 1H), 2.16(m, 1H), 2.67(m, 2H), 4.31(dd, J=9, 5.7 Hz, 1H)

EXAMPLE 2

Under an atmosphere of argon gas, a mxiture composed of 100 mg (0.46 mmol) of 2-hydroxycyclopentadecanone, 142 mg (0.49 mmol) of zinc sulfate, 5 ml of 47% hydrobromic acid and 5 ml of toluene was refluxed with stirring for 22 hours.

This reaction mixture was worked up in the same manner as described in Example 1. Thus, there was obtained 102 mg (74% yield of 2-bromocyclopentadecanone.

EXAMPLE 3

Under an atmosphere of argon gas, a mixture composed of 100 mg (0.42 mmol) of 2-hydroxycyclopentadecanone, 122 mg (0.43 mmol) of zinc sulfate, 5 ml of 47% hydrobromic acid and 5 ml of p-xylene was refluxed with stirring for 22 hours.

This reaction mixture was worked up in the same manner as described in Example 1. Thus, there was obtained 77 mg (61% yield) of 2-bromocyclopentadecanone.

EXAMPLE 4

Under an atmosphere of argon gas, a mxiture composed of 101 mg (0.42 mmol) of 2-hydroxycyclopentadecanone, 130 mg (0.45 mmol) of zinc sulfate, 5 ml of 47% hydrobromic acid and 5 ml of 1,2-dichloroethane was refluxed with stirring for 22 hours.

This reaction mixture was worked up in the same manner as described in Example 1. Thus, there was obtained 29 mg (23% yield) of 2-bromocyclopentadecanone.

What is claimed is:

1. A process for preparing a macrocyclic 2-halogenoketone of the formula

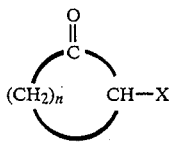

where X is a halogen atom and n is a whole number of 10 to 16, which process comprises reacting a macrocyclic 2-hydroxyketone of the formula

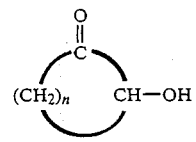

with a halogenating agent, wherein the halogenating agent is one member selected from the group consisting of hydrobromic acid, hydrochloric acid, phosphorus tribromide, phosphorus oxychloride, phosphorus pentachloride, thionyl chloride and thionyl bromide.

2. A process as claimed in claim 1 wherein the halogenating agent is hydrobromic acid.

3. A process as claimed in claim 1 wherein the reaction of the macrocyclic 2-hydroxyketone with the halogenating agent is carried out in the presence of a solvent.

4. A process as claimed in claim 3 wherein the solvent is an organic solvent.

5. A process as claimed in claim 3 wherein the solvent is a two-phase solvent composed of an organic solvent and an aqueous medium.

6. A process as claimed in claim 1 wherein the reaction of the macrocyclic 2-hydroxyketone with the halogenating agent is carried out in the presence of a catalyst.

7. A process as claimed in claim 6 wherein the catalyst is zinc sulfate.

8. The process of claim 1, wherein said 2-hydroxyketone is 2-hydroxycyclopentadecanone.

9. The process of claim 1, wherein said halogenating agent is used in an amount of about 1 to 50 moles per mole of 2-hydroxyketone.

10. The process of claim 4, wherein said organic solvent is an aromatic hydrocarbon or a halogenated hydrocarbon.

11. The process of claim 4, wherein said organic solvent is benzene, toluene, xylene, dichloromethane, or trichloroethane.

12. The process of claim 1, wherein the reaction is carried out at a temperature from room temperature to about 120° C.

13. The process of claim 1, wherein said reaction is carried out at a temperature of from 80° to 110° C.

14. The process of claim 7, wherein said zinc sulfate is used in an amount of from about 0.2 to 2 moles per mole of 2-hydroxyketone.

15. The process of claim 14, wherein said reaction is carried out for a length of time of about 2 to 30 hours.

16. The process of claim 1 wherein said 2-hydroxyketone is 2-hydroxycyclopentadecanone and said 2-halogenoketone is 2-bromocyclopentadecanone.

* * * * *